United States Patent
Armstrong et al.

(10) Patent No.: US 7,711,419 B2
(45) Date of Patent: May 4, 2010

(54) NEUROSTIMULATOR WITH REDUCED SIZE

(75) Inventors: Randolph K. Armstrong, Houston, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 699 days.

(21) Appl. No.: 11/180,745

(22) Filed: Jul. 13, 2005

(65) Prior Publication Data
US 2007/0016263 A1    Jan. 18, 2007

(51) Int. Cl.
*A61N 1/36* (2006.01)

(52) U.S. Cl. .................. 607/2; 607/36; 607/52

(58) Field of Classification Search .................. 607/36, 607/57, 29, 2
See application file for complete search history.

(56) References Cited

U.S. PATENT DOCUMENTS

| | | |
|---|---|---|
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,598,713 A | 7/1986 | Hansjurgens et al. |
| 4,612,934 A | 9/1986 | Borkan |
| 4,702,254 A | 10/1987 | Zabara |
| 4,745,923 A | 5/1988 | Winstrom |
| 4,793,353 A | 12/1988 | Borkan |
| 4,867,164 A | 9/1989 | Zabara |
| 5,025,807 A | 6/1991 | Zabara |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,222,494 A | 6/1993 | Baker, Jr. |
| 5,235,980 A | 8/1993 | Varrichio et al. |
| 5,263,480 A | 11/1993 | Wernicke et al. |

(Continued)

FOREIGN PATENT DOCUMENTS

| | | |
|---|---|---|
| EP | 1145736 | 10/2001 |
| GB | 2079610 | 1/1982 |
| WO | 2003085546 | 4/2004 |

OTHER PUBLICATIONS

Terry, R.S., et al., "The Implantable Neurocybernetic Prosthesis System," Pacing and Clinical Electrophysiology, vol. 14, No. 1, (Jan. 1991), pp. 86-93.
Zabara, J., et al., "Inhibition of Experimental Seizures in Canines by Repetitive Vagal Stimulation," Epilepsia, 33(6), (1992), pp. 1005-1012.

*Primary Examiner*—Carl H Layno
*Assistant Examiner*—Brian T Gedeon
(74) *Attorney, Agent, or Firm*—Williams, Morgan & Amerson, P.C.; Timothy L. Scott

(57) ABSTRACT

A method, system, and an apparatus for providing a therapy neurostimulation signal. The apparatus includes a sealed housing being of a total volume of less than about 14.5 cc and a power supply contained within the sealed housing. The power supply includes a charge capacity of at least about 100 milliAmpHours. The apparatus also includes a controller to control an operation of the power supply and to provide an electrical neurostimulation signal for stimulating a portion of a neural tissue. The apparatus also provides for implementing an interrupt-driven architecture into an implantable medical device.

32 Claims, 8 Drawing Sheets

U.S. PATENT DOCUMENTS

| | | | | |
|---|---|---|---|---|
| 5,269,303 | A | 12/1993 | Wernicke et al. | |
| 5,299,569 | A | 4/1994 | Wernicke et al. | |
| 5,304,206 | A * | 4/1994 | Baker et al. | 607/2 |
| 5,405,363 | A | 4/1995 | Kroll et al. | |
| 5,423,873 | A | 6/1995 | Neubauer et al. | |
| 5,571,150 | A | 11/1996 | Wernicke et al. | |
| 5,690,691 | A | 11/1997 | Chen et al. | |
| 5,757,167 | A * | 5/1998 | Arora et al. | 323/224 |
| 5,836,994 | A | 11/1998 | Bourgeois | |
| 5,861,014 | A | 1/1999 | Familoni | |
| 5,941,906 | A | 8/1999 | Barreras, Sr. et al. | |
| 5,957,956 | A | 9/1999 | Kroll et al. | |
| 5,987,352 | A | 11/1999 | Klein et al. | |
| 5,995,872 | A | 11/1999 | Bourgeois | |
| 6,051,017 | A | 4/2000 | Loeb et al. | |
| 6,083,249 | A | 7/2000 | Familoni | |
| 6,091,992 | A | 7/2000 | Bourgeois et al. | |
| 6,104,955 | A | 8/2000 | Bourgeois | |
| 6,115,635 | A | 9/2000 | Bourgeois | |
| 6,175,764 | B1 | 1/2001 | Loeb et al. | |
| 6,181,965 | B1 | 1/2001 | Loeb et al. | |
| 6,208,894 | B1 | 3/2001 | Schulman et al. | |
| 6,214,032 | B1 | 4/2001 | Loeb et al. | |
| 6,240,316 | B1 | 5/2001 | Richmond et al. | |
| 6,259,951 | B1 | 7/2001 | Kuzma et al. | |
| 6,319,241 | B1 | 11/2001 | King et al. | |
| 6,321,124 | B1 | 11/2001 | Cigaina | |
| 6,327,503 | B1 | 12/2001 | Familoni | |
| 6,356,788 | B2 | 3/2002 | Boveja | |
| 6,360,122 | B1 | 3/2002 | Fischell et al. | |
| 6,466,822 | B1 | 10/2002 | Pless | |
| 6,477,423 | B1 | 11/2002 | Jenkins | |
| 6,522,928 | B2 | 2/2003 | Whitehurst et al. | |
| 6,535,764 | B2 | 3/2003 | Imran et al. | |
| 6,542,776 | B1 | 4/2003 | Gordon et al. | |
| 6,553,263 | B1 | 4/2003 | Meadows et al. | |
| 6,564,102 | B1 | 5/2003 | Boveja | |
| 6,567,703 | B1 | 5/2003 | Thompson et al. | |
| 6,587,724 | B2 | 7/2003 | Mann | |
| 6,587,726 | B2 | 7/2003 | Lurie | |
| 6,591,139 | B2 | 7/2003 | Loftin | |
| 6,606,523 | B1 | 8/2003 | Jenkins | |
| 6,611,715 | B1 | 8/2003 | Boveja | |
| 6,615,081 | B1 | 9/2003 | Boveja | |
| 6,615,085 | B1 | 9/2003 | Boveja | |
| 6,622,038 | B2 | 9/2003 | Varrett et al. | |
| 6,622,041 | B2 | 9/2003 | Terry, Jr. et al. | |
| 6,622,047 | B2 | 9/2003 | Barrett et al. | |
| 6,650,943 | B1 | 11/2003 | Whitehurst et al. | |
| 6,662,052 | B1 | 12/2003 | Sarwal et al. | |
| 6,668,191 | B1 | 12/2003 | Boveja | |
| 6,687,538 | B1 | 2/2004 | Hrdlicka | |
| 6,694,191 | B2 | 2/2004 | Starkweather et al. | |
| 6,708,064 | B2 | 3/2004 | Rezai | |
| 6,731,986 | B2 | 5/2004 | Mann | |
| 6,735,475 | B1 | 5/2004 | Whitehurst | |
| 6,745,077 | B1 * | 6/2004 | Griffith et al. | 607/61 |
| 6,754,536 | B2 | 6/2004 | Swoyer et al. | |
| 6,760,626 | B1 | 7/2004 | Boveja | |
| 6,788,975 | B1 * | 9/2004 | Whitehurst et al. | 607/45 |
| 6,895,278 | B1 | 5/2005 | Gordon | |
| 7,101,642 | B2 * | 9/2006 | Tsukamoto et al. | 429/245 |
| 2003/0055457 | A1 | 3/2003 | MacDonald | |
| 2003/0109903 | A1 | 6/2003 | Berrang et al. | |
| 2003/0204226 | A1 * | 10/2003 | Acosta et al. | 607/48 |
| 2004/0015205 | A1 | 1/2004 | Whitehurst et al. | |
| 2004/0172088 | A1 | 9/2004 | Knudson et al. | |
| 2004/0172089 | A1 | 9/2004 | Whitehurst et al. | |
| 2004/0210270 | A1 | 10/2004 | Erickson | |
| 2005/0065575 | A1 | 3/2005 | Dobak | |
| 2005/0107753 | A1 | 5/2005 | Rezai et al. | |
| 2005/0131486 | A1 | 6/2005 | Boveja et al. | |
| 2005/0131506 | A1 | 6/2005 | Rezai et al. | |
| 2006/0079942 | A1 | 4/2006 | Deno | |
| 2006/0085046 | A1 | 4/2006 | Rezai et al. | |
| 2006/0200205 | A1 * | 9/2006 | Haller | 607/41 |

* cited by examiner

NEUROSTIMULATOR WITH REDUCED SIZE

BACKGROUND OF THE INVENTION

1. Field of the Invention

This invention relates generally to implantable medical devices and, more particularly, to methods, apparatus, and systems for a stimulation device with reduced size.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated in its entirety herein by reference in this specification. Electrical stimulation of the vagus nerve (hereinafter referred to as vagus nerve stimulation therapy or VNS) may be provided by implanting an electrical device underneath the skin of a patient and performing a detection and electrical stimulation process. This type of stimulation is generally referred to as "active," "feedback," or "triggered" stimulation. Alternatively, the system may operate without a detection system once the patient has been diagnosed with epilepsy, and may periodically apply a series of electrical pulses to the vagus (or other cranial) nerve intermittently throughout the day, or over another predetermined time interval. This type of stimulation is generally referred to as "passive," "prophylactic," or "non-feedback" stimulation.

Among the problems associated with state-of-the-art implantable devices is the fact that the size of the devices may cause discomfort or undesired cosmetic effects in many patients. Thus, there is strong desire in the industry to reduce the size of the implantable devices. However, many attempts to reduce the size of the implantable devices have netted sub-par results. Efforts to produce smaller devices often come with the side effect of reduced ability to perform various stimulation-related functions. This may include various calculation functions, data storage functions, communication functions, the quantity and/or quality of therapy that may be delivered, etc.

One subgroup of implantable devices is neurostimulators, which are used to stimulate nerve tissue. Neurostimulators may be being used to neurological and/or sensory disorders. Typically, neurostimulators require greater energy than cardiac stimulators for effective stimulation of the respective target tissues. This produces a greater challenge to reduce size in neurostimulators since larger devices are needed for stimulators with high energy demands.

Designers have attempted to address the problems associated with large devices by providing devices that are smaller, but containing numerous disadvantages. Often, various functions relating to the operations of an implantable medical device may be sacrificed to achieve a smaller profiled device. Other times, when attempting to reduce the size of the implantable device, the battery life of the device is shortened. This may prompt the need for more frequent surgery.

Another disadvantage of some smaller implantable devices is the fact that it may not contain an integral power source sufficiently robust to perform reliable stimulation delivery for a satisfactory period of time. Other small devices may contain the problem of a rechargeable battery with a minimal charge capacity. This may cause the adverse affect of having to recharge the implantable device too often. Some small devices may require integral non-detachable electrodes which may severely limit the ability to target desirable portions of the patient's body. Generally, the devices that contain larger profiles provide a correspondingly greater amount of milliamp-Hours of charge. On the opposite side of the spectrum, very small implantable devices provide for an extremely small amount of milliamp-Hours of charge. Furthermore, small implantable devices provide for mass versus battery capacity that may result in insufficient Ampere-Hours battery capacity. The devices that provide sufficient Ampere-Hours battery capacity generally require large amount of total mass of the device.

The present invention is directed to overcoming, or at least reducing, the effects of one or more of the problems set forth above.

SUMMARY OF THE INVENTION

In one aspect, the present invention comprises an apparatus for providing a therapy neurostimulation signal. The apparatus of the present invention includes a sealed housing having a total volume of less than about 14 cc, more preferably less than about 10 cc, more preferably about 8 cc or less, and a power supply contained within the sealed housing. The power supply includes a charge capacity of at least about 100 milli-AmpHours. The apparatus also includes a controller to control an operation of the power supply and to provide a neurostimulation signal for stimulating a portion of the body tissue of a patient.

In another aspect of the present invention, an implantable medical device (IMD) for providing a therapeutic electrical neurostimulation signal is provided. The IMD includes a multi-function integrated circuit for performing a neurostimulation function. The multi-function integrated circuit includes a boost converter to provide a current for generating a neurostimulation signal. The multi-function integrated circuit also includes a stimulus current regulator to perform a current-regulating function.

In a further aspect of the present invention, an implantable medical device (IMD) for providing a therapeutic electrical neurostimulation signal is provided. The IMD includes a multi-function integrated circuit for performing a neurostimulation function. The multi-function integrated circuit includes a boost converter to provide a current for generating a neurostimulation signal; a stimulus current regulator to perform a current-regulating function; and a switching network operatively coupled to the stimulus current regulator. The switching network is adapted to switch the current to at least one stimulation electrode. The multi-function integrated circuit may also include a supply voltage regulator for regulating a voltage signal from the power supply unit; an internal voltage reference for providing a reference voltage signal for comparison; a telemetry transceiver for providing capability of receiving and sending data from a source external to the implantable medical device; and a reset detector to receive a reset signal and cause a reset of at least a portion of the implantable medical device.

In another aspect of the present invention, a method for providing a therapeutic electrical neurostimulation signal using an IMD is provided. The method comprises providing a controller to perform a neurostimulation function. A multi-function integrated circuit is provided to perform a function relating to said neurostimulation. The controller is placed in a power save mode. The power save mode includes the multi-function integrated circuit performing at least one function relating to said neurostimulation during at least a portion of the time of said power save mode. An interrupt signal relating to performing a task is received. The power save operation mode is exited to perform the task in response to the interrupt.

BRIEF DESCRIPTION OF THE DRAWINGS

The invention may be understood by reference to the following description taken in conjunction with the accompanying drawings, in which like reference numerals identify like elements, and in which.

Figure 1A:
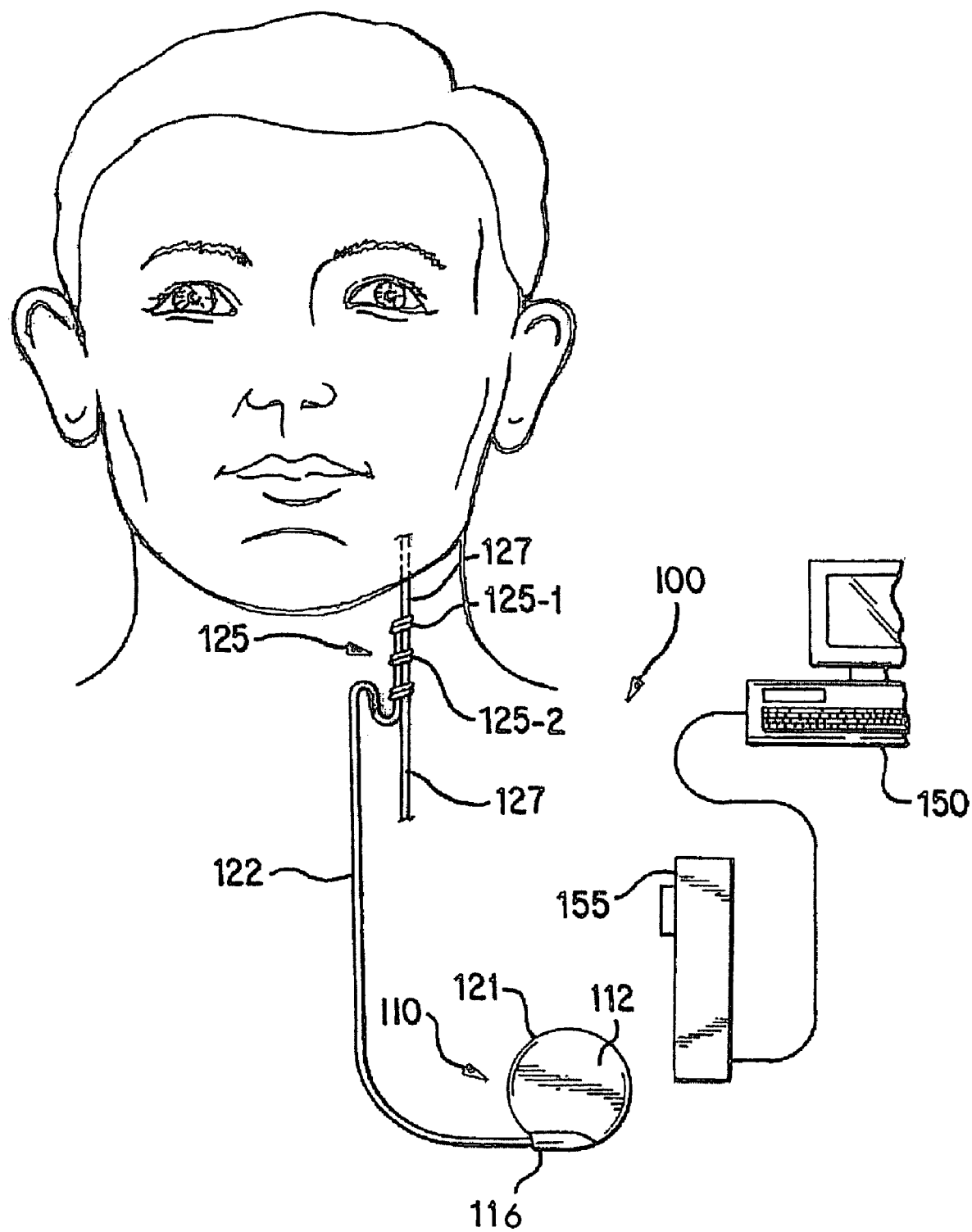
FIGS. 1A-1D provide stylized diagrams of an implantable medical device implanted into a patient's body for providing stimulation to a portion of the patient's body, in accordance with one illustrative embodiment of the present invention.
Figure 1B:
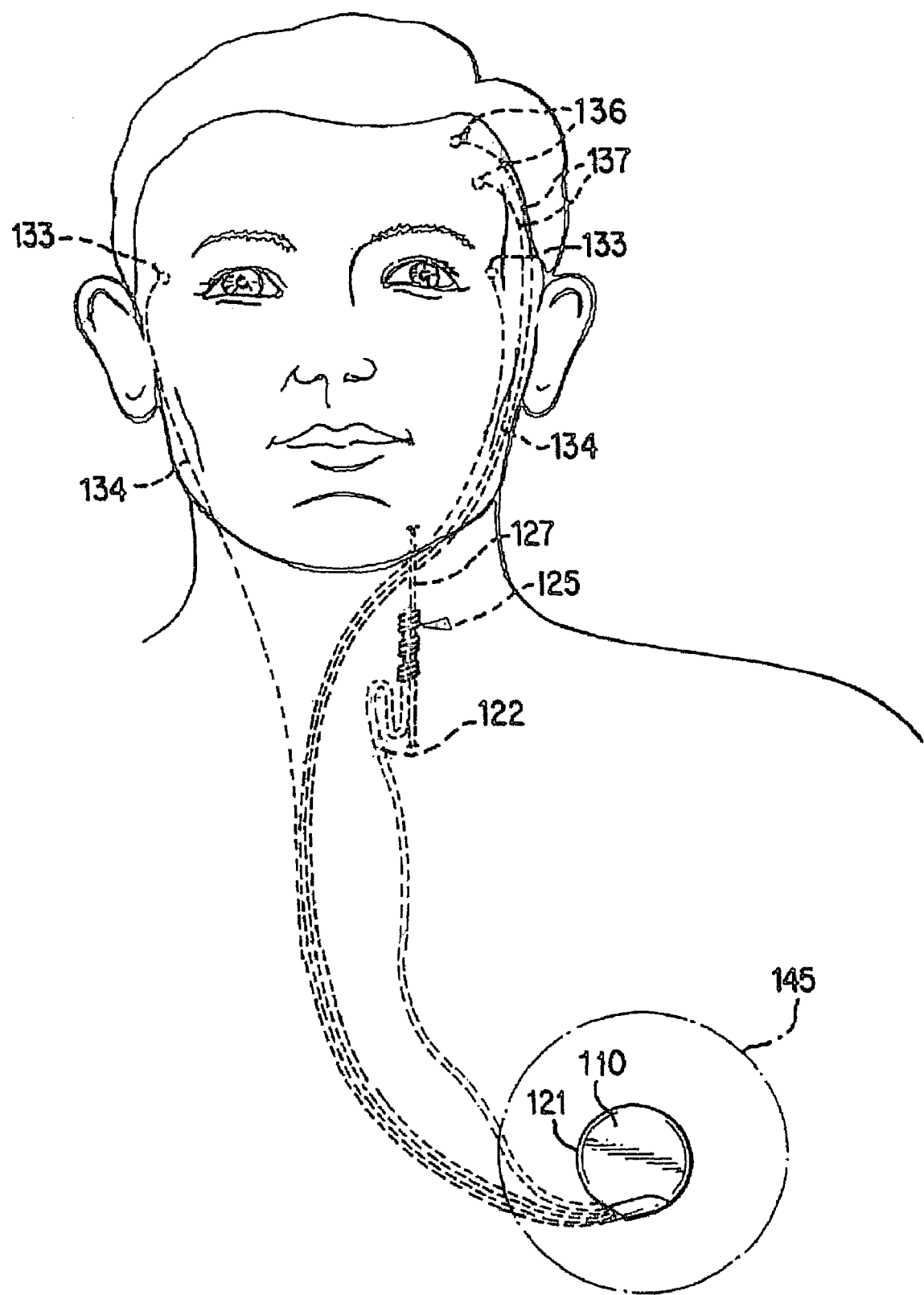
Figure 1C:
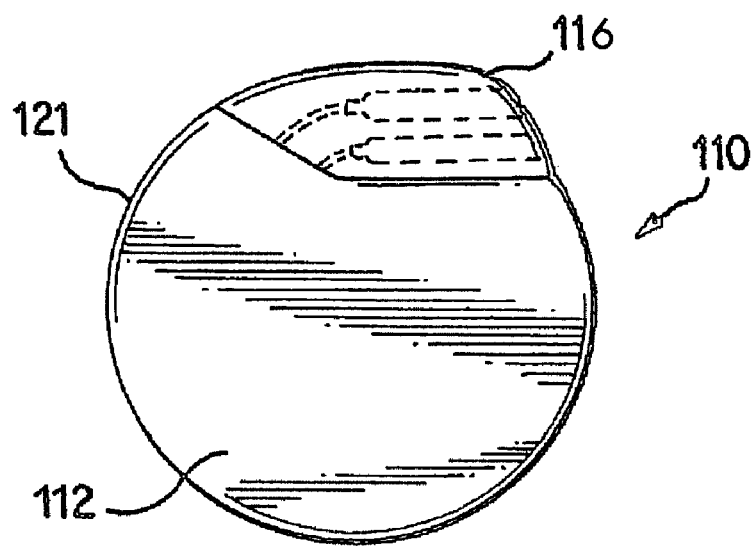
Figure 1D:
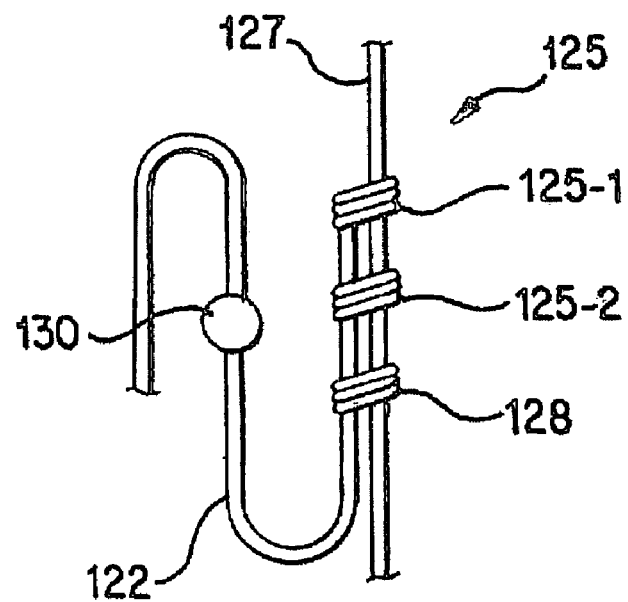

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for various features designed to facilitate the implementation of an implantable medical device in a relatively smaller package. FIGS. 1A-1D depict a stylized implantable medical system 100 for implementing one or more embodiments of the present invention. FIGS. 1A-1D illustrate a generator 110 having main body 112 comprising a case or shell 121 (FIG. 1A) with a connector 116 (FIG. 1C) for connecting to leads 122. The generator 110 is implanted in the patient's chest in a pocket or cavity formed by the implanting surgeon just below the skin (indicated by a dotted line 145, FIG. 1B), similar to the implantation procedure for a pacemaker pulse generator.

A stimulating nerve electrode assembly 125, preferably comprising an electrode pair, is conductively connected to the distal end of an insulated, electrically conductive lead assembly 122, which preferably comprises a pair of lead wires (one wire for each electrode of an electrode pair). Lead assembly 122 is attached at its proximal end to the connector 116 (FIG. 1C) on case 121. The electrode assembly 125 may be surgically coupled to a vagus nerve 127 in the patient's neck. Other cranial nerves may also be used to deliver the electrical neurostimulation signal. The electrode assembly 125 preferably comprises a bipolar stimulating electrode pair (FIG. 1D), such as the electrode pair described in U.S. Pat. No. 4,573,481 issued Mar. 4, 1986 to Bullara. Persons of skill in the art will appreciate that many electrode designs could be used in the present invention. The two electrodes are preferably wrapped about the vagus nerve, and the electrode assembly 125 may be secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue.

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The lead assembly 122 may comprise two distinct lead wires or a coaxial cable whose two conductive elements are respectively coupled to one of the conductive electrode ribbons 125-1 and 125-2. One suitable method of coupling the lead wires or cable to the electrodes comprises a spacer assembly such as that disclosed in U.S. Pat. No. 5,531,778, although other known coupling techniques may be used.

The elastomeric body portion of each loop is preferably composed of silicone rubber, and the third loop 128 (which typically has no electrode) acts as the anchoring tether 128 for the electrode assembly 125.

In certain embodiments of the invention sensors, such as eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a catheter or other suitable means (not shown) and extending along the jaw line through the neck 10 and chest tissue to the electrical pulse generator 110. When included in systems of the present invention, the sensing electrodes 133 may be utilized for detecting rapid eye movement (REM) in a pattern indicative of a disorder to be treated, as described in greater detail below. The detected indication of the disorder can be used to trigger active stimulation.

Other sensor arrangements may alternatively or additionally be employed to trigger active stimulation. Referring again to FIG. 1B, EEG sensing electrodes 136 may optionally be implanted and placed in spaced-apart relation on the skull, and connected to leads 137 implanted and extending along the scalp and temple, and then connected to the electrical pulse generator along the same path and in the same manner as described above for the eye movement electrode leads 134. In addition to active stimulation incorporating sensor elements, other embodiments of the present invention utilize passive stimulation to deliver a continuous, periodic or intermittent electrical signal (each of which constitutes a form of continual application of the signal) to the vagus nerve according to a programmed on/off duty cycle without the use of sensors to trigger therapy delivery. Both passive and active stimulation may be combined or delivered by a single IMD according to the present invention. Either or both modes may be appropriate to treat the particular disorder diagnosed in the case of a specific patient under observation.

The pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

Embodiments of the present invention provide for a novel implementation of an implantable medical device in a relatively small package as compared to various state-of-the-art implantable medical devices. The present invention provides for performing various improvements relating to power conversion, efficiency in performing therapeutic stimulation, etc. Embodiments of the present invention also provide for improvement in the power conversion efficiency relating to supplying power for the internal operations of the implantable medical device. In one embodiment, the power conversion efficiency may relate to the charge available for stimulation as a percentage of the charge drawn from the power supply.

Embodiments of the present invention also provide for a reduction in internal circuit current consumption and reduction in size of components. Embodiments of the present invention provide for a multi-function integrated circuit/chip capable of facilitating integration of various functions performed by the implantable medical device. Utilizing the multi-function integrated circuit provided by embodiments of the present invention, a smaller profile for the implantable device may be achieved while maintaining desirable battery power ratings and stimulation operations.

Figure 2:
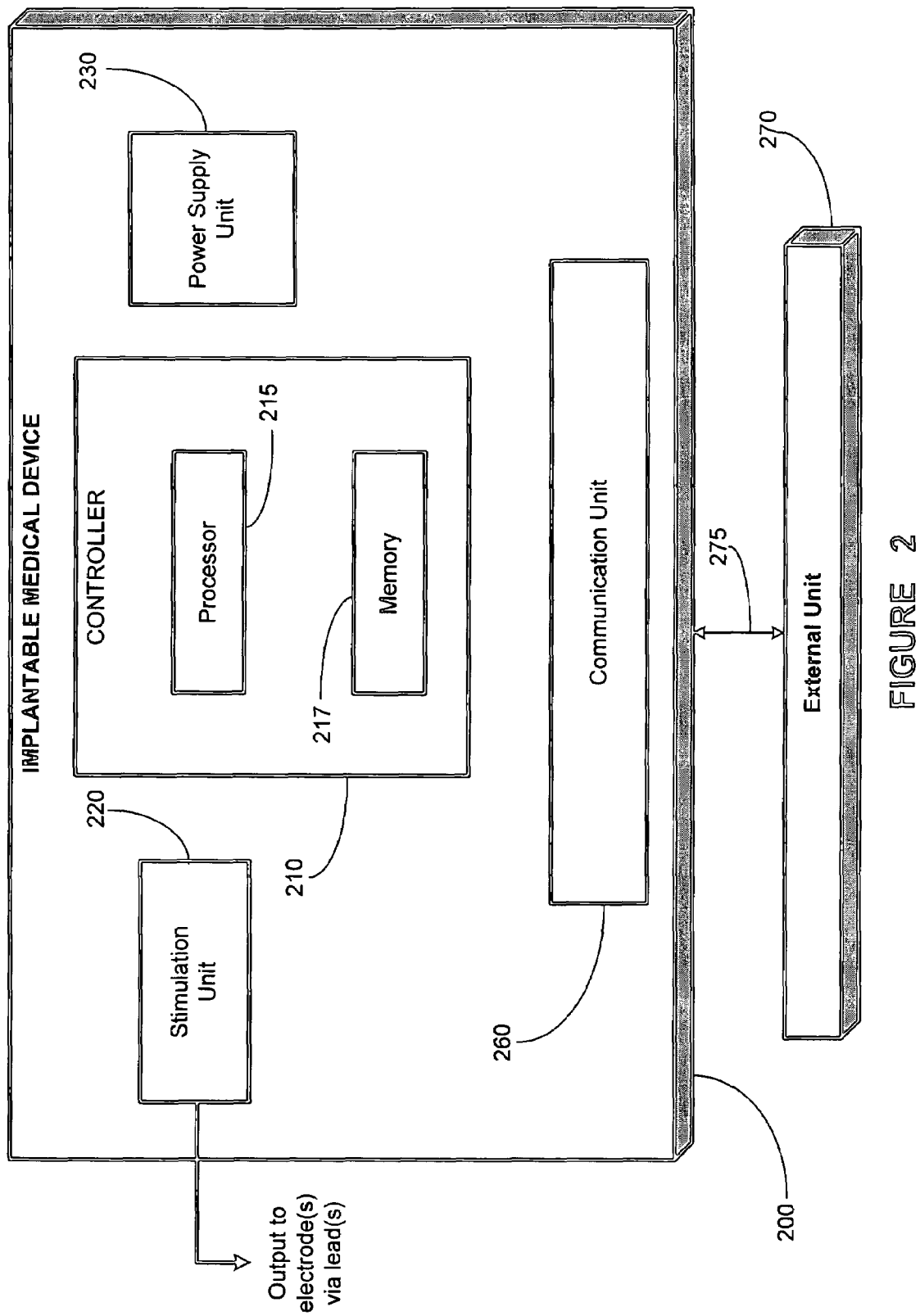
FIG. 2 is a block diagram of an implantable medical device and an external unit that communicates with the implantable medical device, for example to program the implantable medical device, in accordance with one illustrative embodiment of the present invention.

Turning now to FIG. 2, a block diagram depiction of an implantable medical device (IMD), in accordance with one illustrative embodiment of the present invention is illustrated. The IMD 200 may be used to provide electrical stimulation to body tissue, such as nerve tissue, to treat various disorders, such as epilepsy, depression, bulimia, etc. The IMD 200 may be used to treat neuromuscular, neuropsychiatric, cognitive, autonomic, and/or sensory disorders. The IMD 200 may be coupled to various leads, such as lead assembly 122, shown in FIG. 1. Electrical neurostimulation signals from the IMD 200 may be transmitted via the leads 122 to stimulation electrodes associated with the electrode assembly 125. In addition, signals from sensor electrodes associated with the electrode assembly 125 may travel by leads, such as leads 134 and 137, to the IMD 200.

The implantable medical device 200 may comprise a controller 210 that is capable of controlling various aspects of the operation of the IMD 200. The controller 210 is capable of receiving internal data and/or external data and performing stimulation of various portions of the human body. For example, the controller 210 may receive manual instructions from an operator externally, or it may perform stimulation based on internal calculations and protocols programmed into or resident in internal memory 217. The controller 210 is capable of affecting substantially all functions of the IMD 200.

The controller 210 may comprise various components, such as a processor 215, a memory 217, and other structures conventional known to those skilled having benefit of the present disclosure. The processor 215 may comprise one or more microcontrollers, microprocessors, etc., that are capable of performing various executions of software components. The memory 217 may comprise various memory portions where a number of types of data (e.g., internal data, external data instructions, software codes, status data, diagnostic data, etc.) may be stored and retrieved. The memory 217 may comprise random access memory (RAM), dynamic random access memory (DRAM), electrically erasable programmable read-only memory (EEPROM), flash memory, etc. In one embodiment, the memory 217 may comprise RAM and Flash memory components.

The IMD 200 may also comprise a stimulation unit 220. The stimulation unit 220 is capable of generating and delivering a variety of neurostimulation signals to one or more electrodes via leads. A number of leads assemblies 122 may be coupled to the IMD 200. Therapy may be delivered to the lead by the stimulation unit 220 based upon instructions from the controller 210. The stimulation unit 220 may comprise various circuitry, such as stimulation signal generators, and other circuitry that receives instructions relating to the type of stimulation to be performed. The stimulation unit 220 is capable of delivering a controlled current neurostimulation signal over the leads. In one embodiment, the controlled current neurostimulation signal may refer to a prescribed or pre-determined current to a neural tissue of a patient.

The IMD 200 may also comprise a power supply 230. The power supply 230 may comprise a battery, voltage regulators, etc., to provide power for the operation of the IMD 200, including delivering stimulation. The power supply 230 may comprise a power-source battery that in some embodiments is rechargeable. The power supply 230 provides power for the operation of the IMD 200, including electronic operations and the stimulation function. The power supply unit 230, in one embodiment, may comprise a lithium/thionyl chloride cell or, more preferably, a lithium/carbon monofluoride (LiCFx) cell.

The IMD 200 also comprises a communication unit 260 capable of facilitating communications between the IMD 200 and various devices. The communication unit 260 is capable of providing transmission and reception of electronic signals to and from an external unit 270. The external unit 270 may be a device that is capable of programming various modules and stimulation parameters of the IMD 200. In one embodiment, the external unit 270 is a computer system that is capable of executing a data-acquisition program. The external unit 270 may be controlled by a medical professional, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may comprise hardware, software, firmware, and/or any combination thereof. Communications between the external unit 270 and the communication unit 260 may occur via a wireless or other type of communication, illustrated generally by line 275 in FIG. 2.

Figure 3:
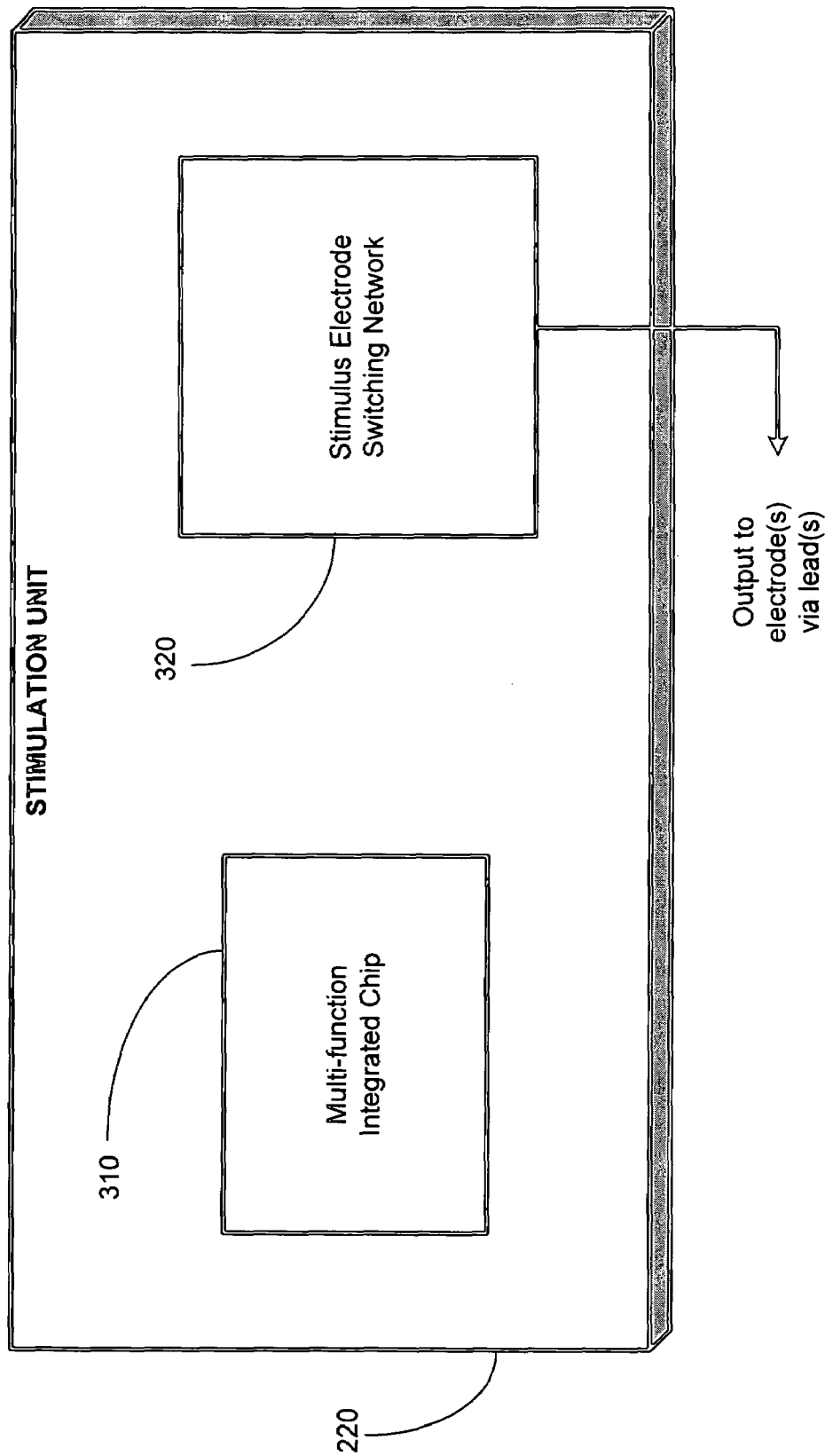
FIG. 3 illustrates a block diagram depiction of one embodiment of the stimulation unit of FIG. 2 comprising a multi-function integrated circuit, in accordance with one embodiment of the present invention.

Turning now to FIG. 3, a block diagram depiction of a stimulation unit in accordance with one embodiment of the present invention is illustrated. The stimulation unit 220 may comprise a multi-function integrated circuit/chip 310. The multi-function integrated circuit/chip 310 may perform various electronic and/or electrical functions to generate and provide electrical neurostimulation signals to electrodes coupled to the IMD 220. Various circuitry, sensors, drivers, logic circuits, firmware, software components, memory, processors, etc. may be implemented into the multi-function integrated circuit chip.

The multi-function integrated circuit/chip 310 is capable of providing control and/or neurostimulation signals to a stimulus electrode switching network 320. The stimulus control switching network 320 is capable of switching various switches, relays, registers, etc. that may be comprised within the IMD 200. The stimulus control switching network 320 is capable of controlling the delivery of the electrical neurostimulation signal. The multi-function integrated circuit/chip 310 may provide control signals to control the switching of the various components of the switching network 320 to deliver specific, targeted neurostimulation signals to predetermined electrodes. More detailed illustrations of the multi-function integrated circuit/chip 310 and the stimulation unit 320, in general, is provided in FIGS. 4 and 5 and accompanying description below.

Figure 4:
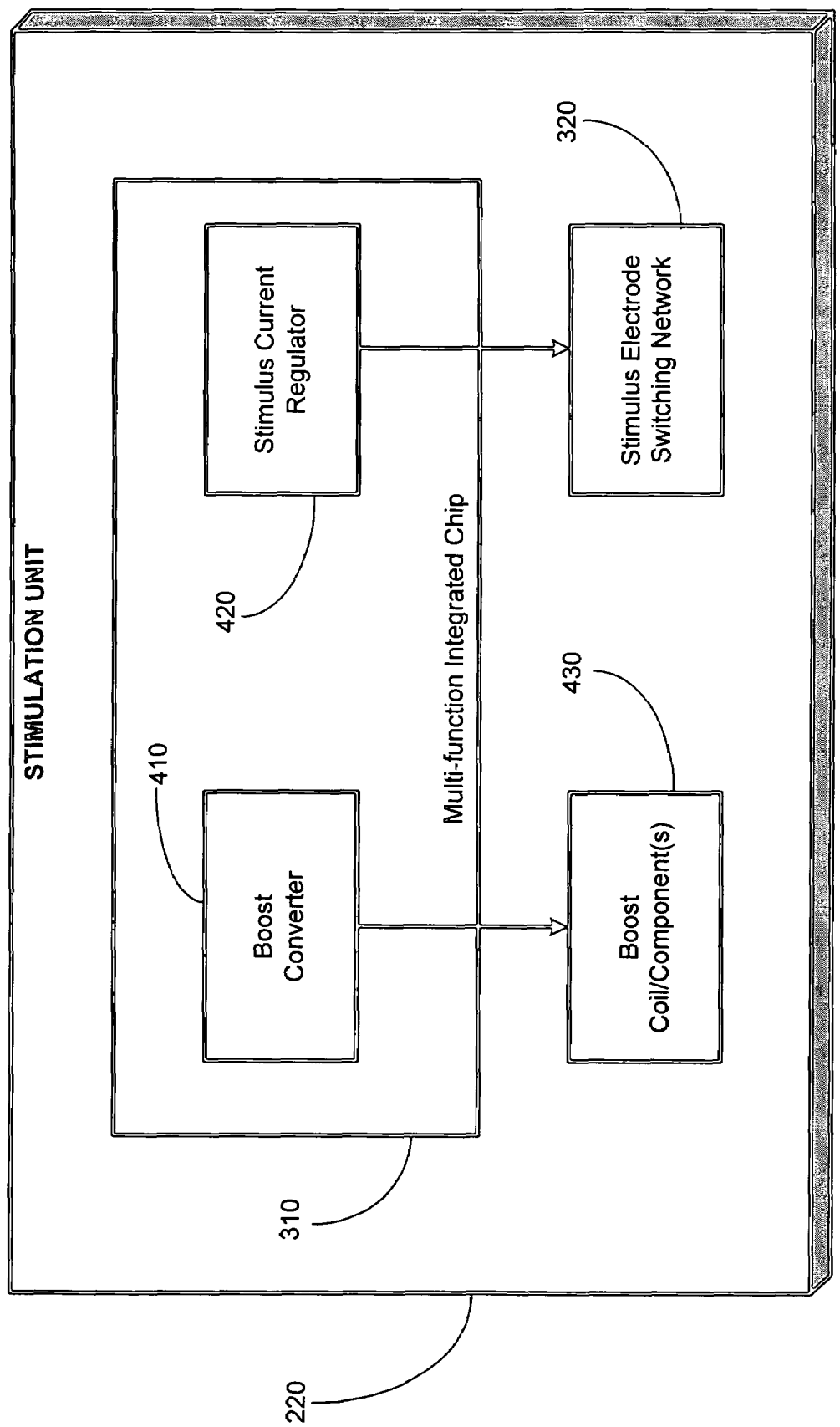
FIG. 4 illustrates a more detailed block diagram depiction of one embodiment of the stimulation unit of FIG. 2, in accordance with an embodiment of the present invention.

Turning now to FIG. 4, a more detailed depiction of the stimulation unit 220 and the multi-function integrated chip 310, in accordance with an illustrative embodiment of the present invention is provided. In one embodiment, the multi-function integrated chip 310 may encompass, among other circuitry, a boost converter 410 and a stimulus current regulator 420. The boost converter 410 may be operatively coupled to a boost coil/component(s) 430. In an alternative embodiment, the boost coil/component(s) 430 may reside within the multi-function integrated chip 310. The boost converter 410 may provide for utilizing energy from the power supply 230 to boost a voltage signal from the power supply at appropriate levels for delivering the electrical neurostimulation signal to a target portion of the patient's body. The boost coil/components 430 comprising part of the stimulation unit 220 may engage the boost converter 410 to convert energy from the power supply, into a deliverable electrical neurostimulation signal.

The boost converter 410, along with the stimulus current regulator 420, may provide for improved efficiency of power conversion from the power supply unit 230. For example, an efficiency of approximately 70% to approximately 95% may be achieved by the novel implementation of boost converter 410 and the stimulus current regulator 420 being integrated into the multi-function integrated circuit chip. The boost converter 410 along with the boost coil/components 430 is capable of boosting a voltage from the power supply 230 to an appropriate charge to provide an electrical neurostimulation.

Employing the configuration illustrated in FIG. 4, the boost converter 410 is more compatible with the boost coil/component(s) 430, thereby promoting efficiency in energy conversion.

The multi-function integrated circuit/chip 310 may also comprise a stimulus current regulator 420. The stimulus current regulator 420 provides for regulating a current of the electrical neurostimulation signal, such that a controlled current electrical neurostimulation signal may be provided by the stimulation unit 220. The stimulus current regulator 420 may provide the current-regulated electrical neurostimulation signal to the stimulus electrode switching network 320. The stimulus electrode switching network 320 may be controlled by the controller 210 such that it is configured to deliver neurostimulation signals to predetermined electrodes. Based upon the configuration of various switches controlled by the stimulus electrode switching network 320, the controlled current electrical neurostimulation signal from the stimulus current regulator 420 may be delivered to various targeted electrodes.

The integration of the boost converter 410 and the stimulus current regulator 420 into the multi-function integrated circuit/chip 310 may provide for a more efficient layout of circuitry in the IMD 220. Consequently, a smaller profile IMD may be produced. The multi-function integrated circuit/chip 310 may comprise various cells that may be programmed as a field programmable configuration or as a pre-programmed device. In one embodiment, the multi-function integrated circuit/chip 310 may be an ASIC chip. However, those skilled in the art will appreciate that the multi-function integrated circuit/chip 310 may comprise various integrated circuitry that may be produced on substrate, such as silicon or other type of solid state material(s). This circuitry may include various programmable devices, programmable objects, ASIC components, logic circuits, firmware components, software components, hardware components, and/or other circuitry that may be integrated into a single integrated circuit chip. The utilization of the multi-function integrated circuit/chip 310 may provide for appreciably smaller profile and/or smaller size of a printed circuit (PC) board used to house the electronics of the IMD 200.

Figure 5:
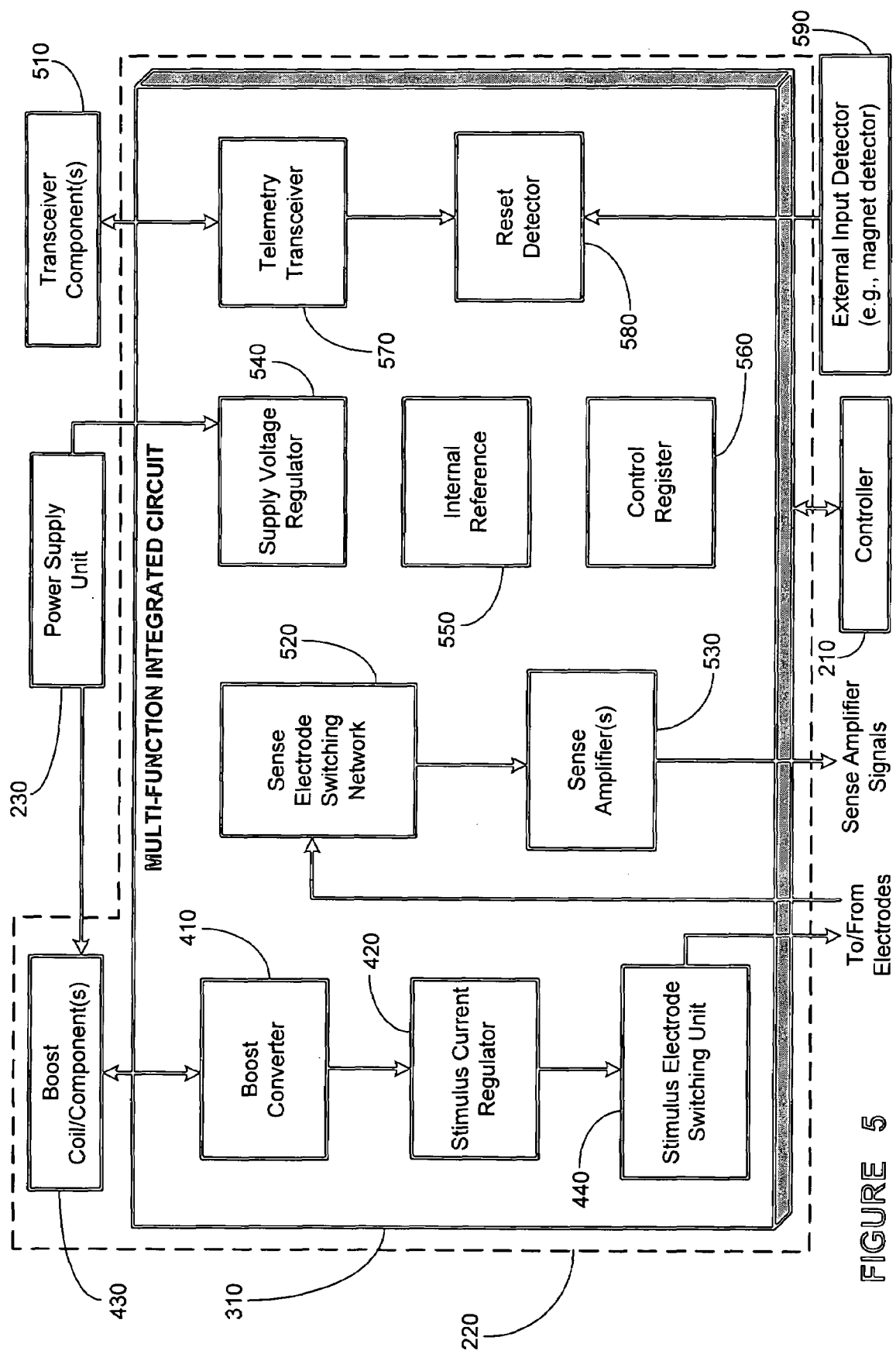
FIG. 5 illustrates a more detailed block diagram depiction of an alternative embodiment of a multi-function integrated circuit of FIG. 3 in accordance with an embodiment of the present invention.

Turning now to FIG. 5, a more detailed depiction of a multi-function integrated circuit/chip 310 is shown, incorporating the functionality of the stimulation unit 220, in accordance with an alternative embodiment of the present invention. In one embodiment, the multi-function integrated circuit/chip 310 may comprise the boost converter 410, the stimulus current regulator 420, and the stimulus electrode switching network 440. Thus, in the embodiment of FIG. 5, the multi-function integrated circuit/chip 310 may directly deliver neurostimulation signals to selected electrodes. This is possible because the embodiment of FIG. 5 integrates the boost converter 410, the stimulus current regulator 420, as well as the stimulus electrode switching network 440 into the multi-function integrated circuit/chip 310, in contrast to the embodiments of FIGS. 3 and 4, in which the stimulus electrode switching network 320 is depicted as off-chip.

Additional circuitry may be implemented into the multi-function integrated chip 310, as shown in FIG. 5. For example, the multi-function integrated circuit/chip 310 may also comprise a sense electrode switching network 520. The sense electrode switching network 520 is capable of switching the configuration of various sensor electrodes. The sense electrode switching network 520 may provide for facilitating transmission of various signals that may be sensed by the sensor electrodes and sent to the IMD 200. The sense electrode switching network 520 may be controlled by the controller 210, which may be in communication with the multi-function integrated circuit/chip 310. The sense electrode switching network 520 may receive data from various electrodes based upon a predetermined configuration, or as provided by a real time adjustment process. Signals from the electrodes may be received by the sense electrode switching network 520, which may then forward the signals to one or more sense amplifiers 530. The sense amplifiers 530 provide conditioning (e.g., amplification, filtering, etc.) of the received sensor signals. In one embodiment, the sense amplifier 530 may also be integrated into the multi-function integrated circuit/chip 310, thereby providing savings in additional real estate on the PC board that is used to house various electronics in the IMD 200.

Referring again to FIG. 5, the multi-function integrated circuit/chip 310 may comprise a supply voltage regulator 540 capable of regulating the voltage of a power signal from the power supply 230. A predetermined regulation of a voltage of a power signal, performed by the supply voltage regulator 540, may provide for a voltage signal for the various operations relating to a number of components of the IMD 200. The output from the supply voltage regulator 540 may also be used to perform a boost conversion to provide controlled current for the therapeutic electrical neurostimulation signal.

In the embodiment depicted in FIG. 5, the multi-function integrated circuit/chip 310 may also comprise an internal reference unit 550. The internal reference unit 550 is capable of providing a plurality of reference signals (e.g., voltage signals and/or current signals) for analysis and comparisons. Furthermore, the multi-function integrated chip 310 may also comprise a control register 560. The control register 560 may comprise various register components (e.g., D-Flip-flops, latches, etc) that may store control information that may be used to control the operations of the IMD 200. The control register 560 may also store other types of data, such as diagnostic data, status data, therapy data, etc. The control register 560 may be accessed by components internal to the IMD 200 and/or components external to the patient's body.

FIG. 5 also shows that the multi-function integrated circuit/chip 310 may also comprise a telemetry transceiver unit 570. The telemetry transceiver unit 570 is capable of sending and/or receiving data via transceiver component(s) 510 in the IMD 200. The transceiver component(s) 510 may include components such as coils, antennae, tuning capacitors, and the like. The telemetry transceiver unit 570 may transmit receive data from a number of sources, such as a controller 210 or sources external to the patient's body. The telemetry transceiver unit 570 may contain a plurality of receivers and/or transmitters capable of sending and receiving data. The telemetry transceiver 570 may also send data to a reset detector 580 also present in the multi-function integrated circuit/chip 310. The reset detector 580 is capable of asserting a signal that is responsive to a detected reset indication. The assertion of the reset signal by reset detector 580 may prompt the reset of various portions of the IMD 200.

Additionally, an external input detector 590 in the IMD 200 may provide data to the reset detector 580, indicating that a reset is desired. The external input detector 590 may receive one or more of a number of types of data detection. For example, the external input detector 590 may comprise a magnet detector that is capable of detecting the presence of a magnetic field. The magnetic field may be caused by the patient placing a magnet proximate to the IMD 200 for performing a reset.

The various components illustrated in FIGS. 3-5 as being implemented into the multi-function integrated circuit/chip 310 may vary, wherein additional or fewer components may be implemented into the multi-function integrated circuit/chip 310. Those skilled in the art would appreciate that one or more of the components shown being integrated into the multi-function integrated chip 310 may be extracted or placed within the multi-function integrated chip 310, and still remain within the spirit and scope of the present invention. Implementation of the various components described above into the multi-function integrated circuit/chip 310 provides for convenience and for savings in PC board real estate, while maintaining adequate functionality and the battery life of a larger version of the IMD 200, in a lower profile package.

The implementation of the various components illustrated in FIG. 5 into the multi-function integrated circuit/chip 310, may also provide for efficient communications and interactions between these components such that a lower amount of current is consumed during the operation of the multi-function integrated chip. Therefore, smaller batteries may be used in the IMD 200 while still maintaining the power supply life of larger versions of the IMD 200.

Other improvements to the circuitry of the IMD 200 may be performed to provide for a lower profile of the IMD 200. For example, various components of the controller 210 may be modified (e.g., such as microcontrollers in the controller 210) such that longer sleep modes or power-save modes may be achieved between execution of various tasks. For example, various processors and/or microcontroller associated with the IMD 200 may be operated in an interrupt-driven architecture. This architecture may call for utilizing short periods of higher speed execution between various low-power or sleep modes. This may provide for reduced average active current consumption of the microcontrollers and/or of various components of the IMD 200. In one embodiment, the microcomputer architecture associated with the controllers 210 may be substantially an interrupt-driven configuration.

Figure 6:
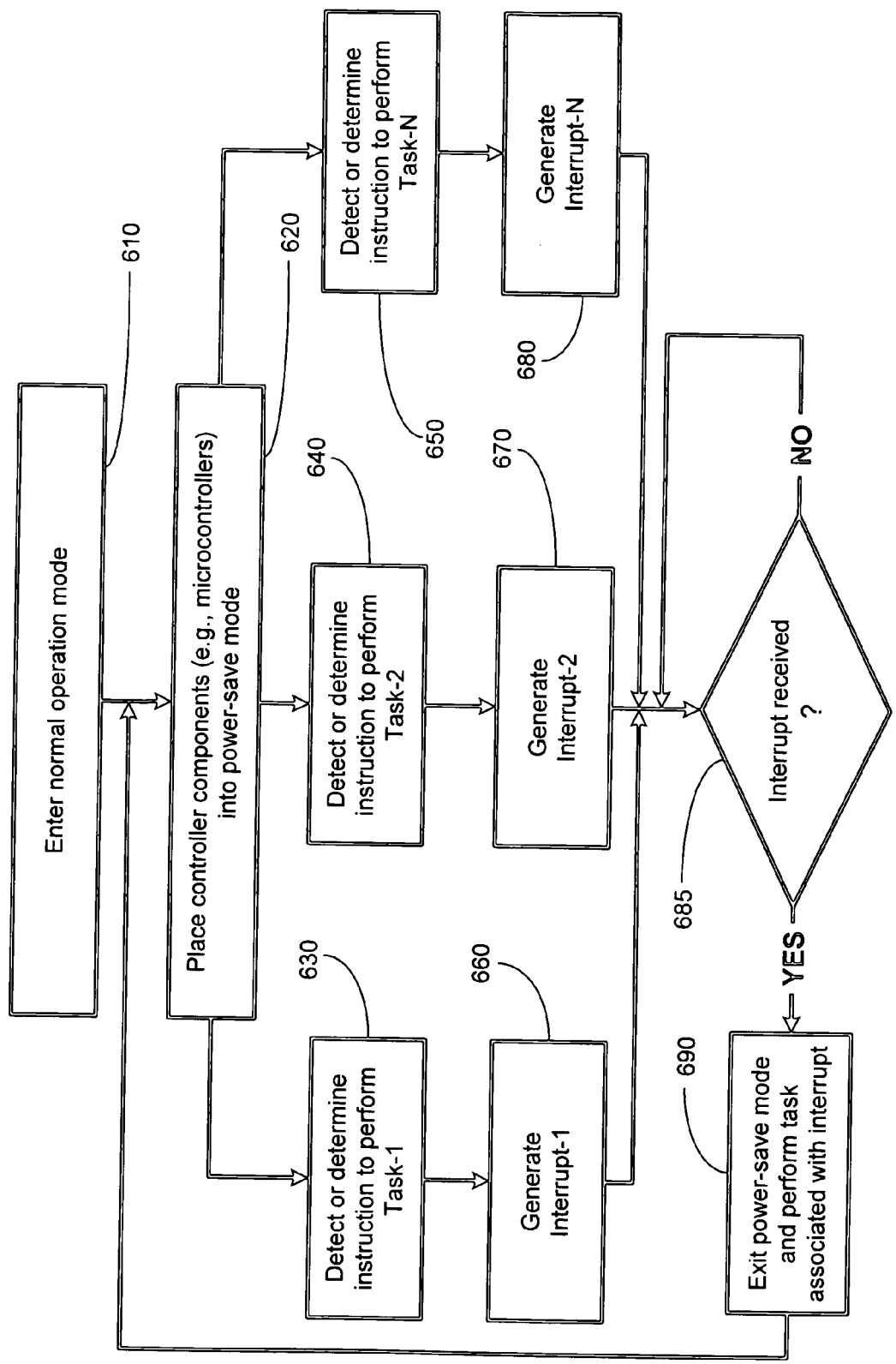
FIG. 6 illustrates a flow chart depiction of an operation of a portion of the controller of FIG. 2, in accordance with one embodiment of the present invention.

Turning now to FIG. 6, a flowchart depiction of the interrupt driven operation of various microcontrollers and/or controllers associated with the controller 210 is illustrated. The IMD 200 may enter into a normal operation mode to provide normal stimulation cycles (block 610). During normal operation, the various components of controller 210 may behave in an interrupt-driven configuration. During an infrequent operation mode, a more active operation of the microcontroller may be implemented. During the more frequent operation mode, the microcontrollers may be placed into a power-save mode, or alternatively, in a sleep mode (block 620). In one embodiment, the microcontroller(s) may perform one or more passive functions while in power-save mode or sleep mode.

In one embodiment, during the power-save mode, the microcontrollers associated with the controller 210 may be in a substantially sleep mode awaiting an interrupt to perform various tasks. For example, the controller 210 may receive an instruction to perform a particular task, e.g., task-1 (e.g., respond to detected electrical event) (block 630). Likewise, the controller 210 may determine that a time period has elapsed and that it is time to perform a task-2 (e.g., store diagnostic data) (block 640). Similarly, the IMD 200 may also be responsive to events related to task-N (e.g., deliver stimulation) (block 650).

In one embodiment, upon detection of an event to perform task-1, an interrupt-1 signal may be generated (block 660). Upon detection of an event to perform task-2, an interrupt-2 signal may be generated (block 670). Similarly, upon detection of an event to perform task-N (wherein N may be any integer), an interrupt-N signal may be generated (block 680). Upon the generation of any one of the interrupt signals (interrupt-1 through interrupt-N signals), a determination may be made whether such an interrupt is received by the processor in the controller 210 (block 685). In another embodiment, in lieu of generating an interrupt signal, the microcontroller may receive an interrupt signal as part of the instruction to perform task-1, task-2, and/or task-N. Upon determination that no interrupt task is received, a continuous monitoring for an interrupt signal may be performed. However, if it is determined that one or more interrupts are received, the microcontrollers may exit the power-save mode and perform a task associated with the particular interrupt signal (block 690). For example, if the interrupt-2 signal is detected, the power-save mode may be exited and the task-2 (e.g., store diagnostic data) is executed.

Subsequent to the execution of a particular task, various component(s) of the controller 210 (e.g., the microcontrollers) may be once again placed into a power-save or a sleep mode, as illustrated in FIG. 6. Therefore, the microcontrollers associated with the controller 210 may generally be placed into a power-save or a sleep mode. When an instruction to perform a particular task and/or an interrupt is received, the components of the controller 210 are placed out of the power-save mode, and the corresponding task is performed. While the controller 210 is in the power-save mode, the multi-function integrated circuit 310 may remain active to optionally perform functions relating to neurostimulation. For example, these functions may include, but are not limited to, boost power conversion, controlled neurostimulation current delivery, or sensing). Utilizing the interrupt-driven architecture described above, substantial power savings may be realized such that extended battery life may be provided even while using smaller components. Therefore, a smaller IMD 200 package may be possible.

Various low leakage characteristics may be realized by utilizing the implementation described above. Additionally, ceramic capacitors, diodes, low-leakage resistors, and/or other low power components may be utilized in order to further reduce power consumption and reduce leakage current, thereby extending the life of the smaller battery. Using the embodiments provided herein, the approximate current consumption of the IMD 200 may be less than approximately 5 micro-Amps when the IMD 200 is not stimulating. The interrupt-driven architecture described herein may provide for the processor associated with the controller 210 to experience an average current draw during off-time of less than approximately 1 micro-Amp. Various portions of the multi-function integrated chip 310 may be implemented to provide for a current consumption less than approximately 10 nano-Amps current consumption when not in use.

Utilizing the embodiments described herein, smaller implantable medical devices may be realized. However, the smaller devices may still operate in a normal manner, delivering various neurostimulation signals and performing various calculations. Hence, smaller sizes, such as the implantable medical device developed by Cyberonics® (Model 103®), which provides for an 8 cc volume with a dimension of 48×33×6.9 mm, and a weight of approximately 16 grams, is made possible while maintaining adequate stimulation operations and battery life (e.g., approximately 1000 milli-AmpHours battery capacity). The concepts disclosed herein may be used to provide for smaller size devices (e.g., a volume of less than approximately 14.5 cc and a weight of less than approximately 25 grams), while maintaining approximately 100 milliAmpHours battery capacity. Other dimensions may be provided for utilizing the concepts described herein while maintaining the spirit and scope of the present invention (e.g., the Model 104® implantable medical device developed by Cyberonics® which utilizes a different connector 116 than that of the Model 103® and provides for a 10 cc volume with a dimension of 48×40×6.9 mm, with a weight of approximately 18 grams). Therefore, more comfortable and smaller implantable medical devices may be provided by implementing embodiments of the present invention. This may provide for greater patient comfort without sacrificing performance and longevity of the power supply implemented in smaller implantable devices.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An implantable medical device (IMD) for implantation in the body of a patient, comprising:
    a sealed housing having a total volume of less than 14.5 cc;
    a power supply contained within said sealed housing for generating a power signal, said power supply comprising a charge capacity of at least about 100 milliAmpHours;
    a controller to control an operation of said power supply and to provide an electrical neurostimulation signal for stimulating neural tissue of the patient,
    a multi-function integrated circuit for generating an electrical neurostimulation signal from said power signal, said multi-function integrated circuit comprising a boost converter to provide a controlled current for generating said electrical neurostimulation signal and a stimulus current regulator to perform a regulation function of said current, and
    a boost coil circuit for interfacing with said boost converter to provide said stimulation current.

2. The implantable medical device of claim 1, wherein said sealed housing comprises a total volume of less than about 10 cc.

3. The implantable medical device of claim 1, wherein said sealed housing comprises a total volume of less than about 8 cc.

4. The implantable medical device of claim 1, wherein said power source comprises a charge capacity of at least about 500 milliAmpHours.

5. The implantable medical device of claim 1, wherein said power source comprises a charge capacity of at least about 1000 milliAmpHours.

6. The implantable medical device of claim 1, wherein said neural tissue is at least one of a right vagus nerve and a left vagus nerve.

7. The implantable medical device of claim 1, wherein said implantable medical device may be used to treat at least one of a neuromuscular, neuropsychiatric, cognitive, autonomic, and a sensory disorder.

8. The implantable medical device of claim 1 wherein implantable medical device may be used to treat a disorder from a group consisting of epilepsy, depression, and bulimia.

9. The implantable medical device of claim 1, wherein the implantable medical device comprises a stimulating current consumption when said implantable medical device provides said electrical neurostimulation signal, and a non-stimulating current consumption, and said implantable medical device is characterized by a non-stimulating current consumption of less than about 5 micro-Amps.

10. The implantable medical device of claim 9, wherein the current consumption of said implantable medical device is characterized by a non-stimulating current consumption of less than about 1 micro-Amp.

11. The implantable medical device of claim 1, wherein said controller comprises a stimulation unit, said stimulation unit comprising the multi-function integrated circuit.

12. The implantable medical device of claim 1, wherein said stimulus current regulator provides a controlled current neurostimulation signal.

13. The implantable medical device of claim 1, wherein said boost converter and said stimulus current regulator provide for an efficiency in converting energy from said power supply to stimulation energy, from a range of about 70 percent to about 95 percent.

14. The implantable medical device of claim 11, wherein said multi-function integrated circuit comprises a switching network operatively coupled to said stimulus current regulator and operating to switch said stimulating current to at least one stimulation electrode.

15. The implantable medical device of claim 11, wherein said multi-function integrated circuit further comprises:
a sensor electrode switching network to switch data from at least one sensor electrode; and
at least one sense amplifier to condition said data from said sensor electrode.

16. The implantable medical device of claim 11, wherein said multi-function integrated circuit further comprises:
a supply voltage regulator for regulating a voltage of the power signal from said power supply unit; and
an internal reference for providing a voltage reference signal for comparison selected from the group consisting a voltage regulator and a current regulator.

17. The implantable medical device of claim 11, wherein said multi-function integrated circuit further comprises:
a telemetry transceiver for providing receiving and sending data from a source external to said multi-function integrated chip; and
a reset detector to receive a reset signal and cause a reset of at least a portion of said implantable medical device.

18. The implantable medical device of claim 1, further comprising a reset detector to receive a reset signal and cause a reset of at least a portion of said implantable medical device.

19. The implantable medical device of claim 1, further comprising a magnet detector to determine the presence of a magnet proximate to said implantable medical device.

20. The implantable medical device of claim 1, wherein said controller comprises a processor being implemented in an interrupt driven architecture.

21. The implantable medical device of claim 20, wherein said processor requires an operating current of less than about 1 micro-Amp when not executing instructions.

22. An implantable medical device (IMD) comprising a power supply for generating a power signal, a multi-function integrated circuit for generating an electrical neurostimulation signal from said power signal, said multi-function integrated circuit comprising a boost converter to provide a controlled current for generating said electrical neurostimulation signal and a stimulus current regulator to perform a regulation function of said current, the IMD further comprising a boost coil circuit for interfacing with said boost converter to provide said stimulation current.

23. The implantable medical device of claim 22, wherein said multi-function integrated circuit further comprises a switching network operatively coupled to said stimulus current regulator and operating to switch said current to at least one stimulation electrode.

24. The implantable medical device of claim 22, wherein said multi-function integrated circuit further comprises:
a sensor electrode switching network to switch data from at least one sensor electrode; and
at least one sense amplifier to condition said data from said sensor electrode.

25. The implantable medical device of claim 22, wherein said multi-function integrated circuit further comprises:
a telemetry transceiver for receiving and sending data from a source external to said implantable medical device and a reset detector to receive a reset signal and cause a reset of at least a portion of said implantable medical device.

26. The implantable medical device of claim 22, further comprising:
a sealed housing having a total volume of less than about 14.5 cc;
a power supply contained within said sealed housing, said power supply comprising a charge capacity of greater than about 100 milliAmpHours; and
a controller to control an operation of said power supply and to provide said electrical neurostimulation signal for stimulating a neural tissue of a patient.

27. An implantable medical device (IMD) comprising a power supply for generating a power signal, a multi-function integrated circuit for generating an electrical neurostimulation signal, said multi-function integrated circuit comprising:
a boost converter to provide a controlled current for generating said electrical neurostimulation signal;
a stimulus current regulator to regulate said current;
a switching network operatively coupled to said stimulus current regulator and operating to switch said current to at least one stimulation electrode;
a supply voltage regulator for regulating a voltage of said power signal from said power supply unit;
an internal voltage reference for providing a reference voltage signal for comparison;
a telemetry transceiver for receiving and sending data from a source external to said implantable medical device; and
a reset detector to receive a reset signal and cause a reset of at least a portion of said implantable medical device,
the IMD further comprising a boost coil circuit for interfacing with said boost converter to provide said stimulation current.

28. The implantable medical device of claim 27, further comprising:
a sensor electrode switching network to switch data from at least one sensor electrode;
at least one sense amplifier to condition said data from said sensor electrode; and
a register for registering data.

29. The implantable medical device of claim 27, further comprising ceramic capacitors.

30. The implantable medical device of claim 27, wherein said multi-function integrated circuit is coupled to a printed circuit board in a sealed housing of a total volume of less than about 14.5 cc.

31. A method for performing neurostimulation using an implantable medical device (IMD), comprising:
providing a controller to perform a function relating to said neurostimulation;

providing a multi-function integrated circuit comprising a boost converter to provide a controlled current to perform a function relating to said neurostimulation;

providing a boost coil circuit for interfacing with said boost converter to provide said stimulation current;

placing said controller in a power save mode, said power save mode comprising said multi-function integrated circuit performing at least one function relating to said neurostimulation during at least a portion of a time period during said power save mode;

receiving an interrupt relating to performing a task; and exiting said power save operation mode to perform said task in response to said interrupt.

32. The method of claim 29, further comprising:

determining whether the performance of said task is substantially complete; and entering said power save mode in response to a determination that said performance of said task is substantially complete.

\* \* \* \* \*